United States Patent [19]

Torii et al.

[11] Patent Number: 4,861,768

[45] Date of Patent: Aug. 29, 1989

[54] 2 β-SUBSTITUTED THIOMETHYLPENICILLIN DERIVATIVES AND THEIR PREPARATION AND USE

[75] Inventors: Sigeru Torii; Hideo Tanaka; Motoaki Tanaka, all of Okayama; Shozo Yamada, Honjye; Akira Nakai, Okayama; Hisashi Ohbayashi, Honjyo; Hideo Tanaka; Motoaki Tanaka, both of Okayama; Shozo Yamada, Honjyo; Akira Nakai, Okayama; Hisashi Ohbayashi, Honjyo, all of Japan

[73] Assignee: Taiho Pharmaceutical Company, Limited, Tokyo, Japan

[21] Appl. No.: 16,114

[22] Filed: Feb. 18, 1987

[30] Foreign Application Priority Data

Feb. 27, 1986 [JP] Japan ................................. 61-43763
Nov. 10, 1986 [JP] Japan ............................... 61-268137

[51] Int. Cl.[4] ................. A61K 31/425; C07D 499/00
[52] U.S. Cl. ..................................... 514/195; 540/304; 540/310; 514/196; 514/197; 514/200
[58] Field of Search ............... 540/304, 310; 514/195, 514/196, 197, 200

[56] References Cited

U.S. PATENT DOCUMENTS

| 3,954,732 | 5/1976 | Kamiya et al. | 540/338 |
| 4,164,497 | 8/1979 | Kamiya et al. | 540/338 |
| 4,218,374 | 8/1980 | Kamiya et al. | 540/304 |

FOREIGN PATENT DOCUMENTS

| 49-69694 | 7/1974 | Japan . |
| 49-75589 | 7/1974 | Japan . |
| 58-154587 | 9/1983 | Japan . |
| 2157286 | 10/1985 | United Kingdom . |

OTHER PUBLICATIONS

English et al., "Antimicrobial Agents & Chemotherapy", vol. 14, No. 3, Sep. 1978, pp. 414–419.
Hall, T. W. et al., "Recent Advances in the Chemistry of β-Lactam Antibiotics", 1985, pp. 242–254.
Gottstein et al., J. Med Chem., 1981, 24, 1531–1534.
J. Med. Chem., 1985, 28, 518–522, Gottstein et al.
Chemical Abstracts, vol. 100, No. 11, Mar. 12th, 1984, p. 256, No. 85504y.

Primary Examiner—Werren B. Lone
Assistant Examiner—Vera C. Clarke
Attorney, Agent, or Firm—Armstrong, Nikaido Marmelstein Kubovcik & Murray

[57] ABSTRACT

Disclosed is a penicillin derivative of the formula:

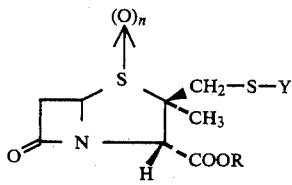

wherein n is an integer of 0, 1 or 2; Y is a cyano group, a lower acyl group, a mono- or di-lower alkylthiocarbamoyl group,

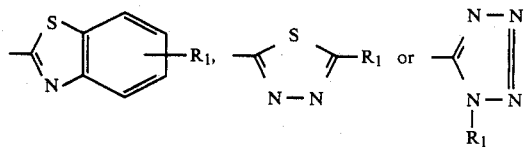

wherein $R_1$ is a hydrogen atom, a lower alkyl group, a phenyl group, a group $-(CH_2)_m-OR_2$ or $-(CH_2)_m COOR_2$ (m is an integer of 1 to 6 and $R_2$ is a hydrogen atom or a penicillin carboxyl ester-forming group which is commonly used for penicillin derivatives) or a phenyl group substituted by at least one member selected from the class consisting of lower alkyl group, halogen atom and lower alkoxy group; and R is a hydrogen atom or a penicillin carboxyl ester-forming group, or a salt thereof. They are useful as β-lactamase inhibitors.

26 Claims, No Drawings

2 β-SUBSTITUTED THIOMETHYLPENICILLIN DERIVATIVES AND THEIR PREPARATION AND USE

The present invention relates to penicillin derivatives, and more particularly to 2β-substituted thiomethylpenicillin derivatives. The invention also relates to a process for preparing said derivatives and to the use thereof, especially pharmaceutical compositions containing said derivatives.

Of the commercially available antibiotics, β-lactam type antibiotics having a β-lactam ring, namely penicillins and cephalosporins, are best known and most frequently used. Although widely used as useful chemotherapeutic agents, the β-lactam type antibiotics cannot produce satisfactory effects on some microorganisms because of the resistance of the microorganisms to these antibiotics. This resistance is usually attributable to the β-lactamase produced by the microorganism. The β-lactamase is an enzyme which cleaves the β-lactam ring of the β-lactam type antibiotic, thereby causing the antibiotic to lose its antimicrobial activity For this reason, the action of β-lactamase must be inhibited so as to enable the β-lactam type antibiotic to produce satisfactory effects. The elimination or inhibition of the β-lactamase activity can be achieved by means of β-lactamase inhibitors, which are used conjointly with the β-lactam type antibiotic to increase the antimicrobial activity of the antibiotic.

Recently, as much emphasis has been placed on the development of β-lactamase inhibitors as on the development of antibiotics. β-Lactamase inhibitors having various chemical structures have been developed thus far. Taking inhibitors containing the penicillin nucleus as examples, the compound of structural formula (A) (U.S. Pat. No. 4,234,579) and the compound of structural formula (B) (European Patent No. 97446) (shown below) are known. However, neither of them is fully satisfactory and researchers are hard at work for the development of superior β-lactamase inhibitors.

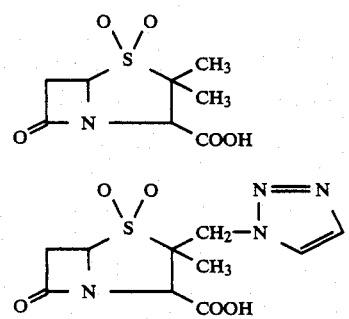

It is an object of the present invention to provide novel compounds having β-lactamase inhibitory activity.

It is another object of the invention to provide processes for preparing the same.

It is a further object of the invention to provide pharmaceutical compositions which produce excellent β-lactamase inhibitory effects.

It is an additional object of the invention to provide compositions which, when combined with β-lactam type antibiotics, can increase the antibacterial activity of the antibiotics.

The present invention provides penicillin derivatives of the following formula (I) and their salts.

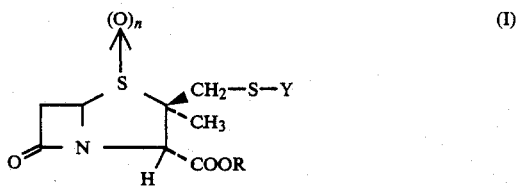

wherein n is an integer of 0, 1 or 2: Y is a cyano group, a lower acyl group, a mono- or di-(lower alkyl)thiocarbamoyl group,

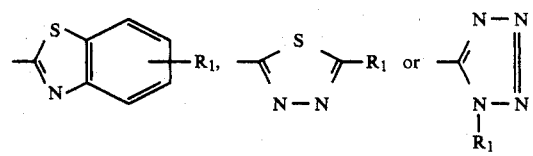

wherein $R_1$ is a hydrogen atom, a lower alkyl group, a phenyl group, a group $-(CH_2)_m-OR_2$ or $-(CH_2)_m COOR_2$ (m is an integer of 1 to 6 and $R^2$ is a hydrogen atom, or a penicillin carboxyl ester-forming group which is commonly used for penicillin derivatives) or a phenyl group substituted by at least one member selected from the class consisting of lower alkyl group, halogen atom and lower alkoxy group; and R is a hydrogen atom or a penicillin carboxyl ester-forming group.

The present inventors synthesized a large variety of compounds and investigated them for β-lactamase inhibitory activity. As a result, we found that novel penicillin derivatives having a thiomethyl group in the 2-position of the penicillin nucleus exert high inhibitory effects on β-lactamases and accomplished the present invention.

In the specification and particularly in regard to the compounds of the formula (I), the lower acyl group represented by Y includes an acyl group containing 2 to 6 carbon atoms, such as acetyl, propionyl, butyryl, pentanoyl, hexanoyl and so on. The mono- or di(lower alkyl)thiocarbamoyl group, also represented by Y, includes a thiocarbamoyl group having one or two lower alkyl groups of 1 to 6 carbon atoms on the nitrogen atom thereof, such as methylthiocarbamoyl, ethylthiocarbamoyl, propylthiocarbamoyl, butylthiocarbamoyl, pentylthiocarbamoyl, hexylthiocarbamoyl, dimethylthiocarbamoyl, methylethylthiocarbamoyl, diethylthiocarbamoyl, and so on. The lower alkyl group includes a straight-chain or branched-chain alkyl group of 1 to 6 carbon atoms, such as methyl, ethyl, propyl, isopropyl, butyl, sec-butyl, tert-butyl, pentyl, hexyl and so on.

As the halogen atom as a substituent on the phenyl group, there may be mentioned fluorine, chlorine, bromine or iodine. As the lower alkoxy group as a substituent on the phenyl group, there may be mentioned straight-chain or branched-chain lower alkoxy groups of 1 to 6 carbon atoms, such as methoxy, ethoxy, isopropoxy, butoxy, tert-butoxy, pentyloxy, hexyloxy, and so on.

The term "penicillin carboxyl ester-forming group", as represented by R and $R_2$, is used herein to mean any known ester residue group used in the synthesis of known penicillin derivatives or any group which is capable of forming esters which is readily hydrolyzed in the vivo. As examples of such penicillin carboxyl ester-forming groups, there may be mentioned the groups which are conventionally used in the β-lactam antibiotics, as mentioned in Japanese Unexamined Patent Publication (Kokai) No. 49-81380 and H. E. Flynn (ed.) Cephalosporins and Penicillins, Chemistry and Biology (Academic Press, 1972) and other literature. Thus, typical examples thereof include straight-chain or branched-chain $C_{1-6}$ alkyl groups such as methyl, ethyl, propyl, isopropyl, tert-butyl, pentyl, hexyl, etc.; $C_{2-7}$ alkoxymethyl groups such as methoxymethyl, ethoxymethyl, propyloxymethyl, isopropyloxymethyl, butoxymethyl, hexyloxymethyl, etc.; $C_{3-8}$ alkylcarbonyloxymethyl groups such as methylcarbonyloxymethyl, ethylcarbonyloxymethyl, butylcarbonyloxymethyl, hexylcarbonyloxymethyl, etc.; $C_{4-9}$ alkylcarbonyloxyethyl groups such as methylcarbonyloxyethyl, ethylcarbonyloxyethyl, butylcarbonyloxyethyl, pivaloyloxyethyl, etc.; ($C_{5-7}$ cycloalkyl)carbonyloxymethyl groups such as cyclopentylcarbonyloxymethyl, cyclohexylcarbonyloxymethyl, cycloheptylcarbonyloxymethyl, etc., $C_{9-14}$ benzylcarbonyloxyalkyl groups such as benzylcarbonyloxymethyl, benzylcarbonyloxyethyl, bezylcarbonyloxypropyl, benzylcarbonyloxybutyl, etc.; $C_{3-8}$ alkoxycarbonylmethyl groups such as methoxycarbonylmethyl, ethoxycarbonylmethyl, propyloxycarbonylmethyl, hexyloxycarbonylmethyl, etc.; $C_{4-9}$ alkoxycarbonylethyl groups such as methoxycarbonylethyl, ethoxycarbonylethyl, propyloxycarbonylethyl, butoxycarbonylethyl, hexyloxycarbonylethyl, etc.; halogenated $C_{1-6}$ alkyl groups as substituted by 1 to 3 halogen atoms such as chloromethyl, 2,2-dibromoethyl, trichloroethyl, etc.; $C_{1-6}$ alkoxy- or nitro-substituted or unsubstituted benzyl groups such as p-methoxybenzyl, p-ethoxybenzyl, o-nitrobenzyl, p-nitrobenzyl, etc.; benzhydryl; trityl; $C_{4-6}$ cyclic ether groups such as tetrahydrofuranyl, tetrahydropyranyl, etc.; halogenosilyl groups such as dimethylchlorosilyl, trichlorosilyl, etc.; (5-$C_{1-6}$ alkyl- or phenyl-substituted and unsubstituted-2-oxo-1,3-dioxoden-4-yl)methyl groups such as (2-oxo-1,3-dioxoden-4-yl)methyl, (5-methyl-2-oxo-1,3-dioxoden-4-yl)methyl, (5-phenyl-2-oxo-1,3-dioxoden-4-yl)methyl, etc.; $C_{8-13}$ benzoyloxyalkyl groups such as benzoyloxymethyl, benzoyloxyethyl, benzoyloxypropyl, benzoyloxybutyl, etc.; lower alkylsilyl groups containing 1 to 6 carbon atoms such as trimethylsilyl, tert-butyldimethylsilyl, etc.; and dialkoxyalkyl groups of 1 to 6 carbon atoms such as dimethoxymethyl, diethoxymethyl, ethoxymethoxyethyl, etc.

The penicillin carboxyl ester-forming group, as represented by R or $R_2$, includes the carboxyl-protecting groups which are useful in the synthesis of penicillin compounds and the groups used in the production of pharmaceutically acceptable penicillin esters. The pharmaceutically acceptable ester having such a group is readily hydrolyzed in vivo and is harmless because it is rapidly decomposed in the blood or tissue of mammalian animals to yield the corresponding acid of the formula (I) in which R is a hydrogen atom. Generally in the synthesis of penicillin compounds, various carboxy-protecting groups are used to protect the carboxyl groups which are not to be involved in the contemplated reaction. In selecting a carboxy-protecting group, it is advisable to see to it that the protective group per se is sufficiently stable in the reaction and does not cause cleavage of the β-lactam ring in its subsequent removal. Most commonly used carboxy-protecting groups are p-nitrobenzyl, benzhydryl, trichloroethyl, trichlorosilyl, tetrahydropyranyl, and so on. Examples of the pharmaceutically acceptable ester residues are phthalidyl, crotonolacton-4-yl, γ-butyrolacton-4-yl, (2-oxo-1,3-dioxoden-4-yl)methyl, and so on.

The salt according to the present invention is preferably a pharmaceutically acceptable salt including salts of alkali metals such as sodium, potassium, lithium, etc., salts of alkaline earth metals such as calcium, magnesium, etc., and salts of various amines. The amines may for example be lower alkyl amines such as trimethylamine, hydroxy-lower alkylamines such as 2-hydroxyethylamine, bis(2-hydroxyethyl)amine, tris(2-hydroxyethyl)amine, etc., cycloalkylamines such as bicyclohexylamine, etc., benzylamines such as N-methylbenzylamine, N-ethylbenzylamine, N-benzyl-β-phenethylamine, N,N-dibenzylethylenediamine, dibenzylamine, etc., heterocyclic amines such as morpholine, N-ethylpiperidine, etc., procaine, basic amino acids such as arginine, lysine, and so on.

The penicillin derivatives of the present invention and pharmaceutically acceptable salts thereof are all novel compounds and have β-lactamase inhibitory properties, hence being useful as β-lactamase inhibitors.

The penicillin derivatives of the invention, when used in combination with a known β-lactam type antibiotic, can increase the antimicrobial activity of the β-lactam type antibiotic.

Examples of antibiotics which can be used conjointly with the compounds of the present invention are β-lactam antibiotics which exhibit antibacterial activity against gram-positive or gram-negative bacteria and include commonly used penicillins such as ampicillin, amoxicillin, hetacillin, ciclacillin, mecillinam, carbenicillin, sulbenicillin, ticarcillin, piperacillin, apalcillin, methicillin, mezlocillin, etc. and salts thereof; esters of penicillins such as bacampicillin, carindacillin, talampicillin, carfecillin and pivmecillinam; cephalosporins such as cephaloridine, cephalothin, cephapirin, cephacetrile, cefazolin, cephalexin, cefradine, cefotiam, cefamandole, cefuroxime, cefoxitin, cefmetazole, cefsulodin, cefoperazone, cefotaxime, ceftizoxime, cefmenoxime, latamoxef, cefaclor, cefroxadine, cefatrizine, cefadroxil, cephaloglycin, etc. and salts thereof. The β-lactam antibiotic is usually used in an amount of about 0.1 to about 10 parts by weight, preferably about 0.2 to about 5 parts by weight, per part by weight of the compound of the invention.

The penicillin derivative of the present invention, or a pharmaceutically acceptable salt thereof, and a suitable β-lactam antibiotic can be independently administered. Alternatively, the derivative or the salt thereof is mixed with the β-lactam antibiotic to form a preparation which is orally or parenterally administered. Usually, the latter administration method is preferred. Thus the derivatives of the invention and pharmaceutically acceptable salts thereof can be used for treating bacterial infections and infectious disease in humans and other animals, especially mammalian animals.

The composition of the present invention may be made into tablets, pills, capsules, granules, powders, syrups, lozenges, solutions, suspensions, etc. for oral administration, and aqueous solutions, suspensions, or water-soluble preparations for intravenous, subcutaneous or intramuscular injections, in a conventional manner.

Carriers useful in formulating such preparations are commonly used pharmaceutically acceptable non-toxic carriers such as gelatin, lactose, starch, magnesium stearate, talc, vegetable oil, animal oil, polyalkylene glycol, and so on. The carrier may be used with other additives such as diluents, binders, buffer agents, preservatives, glazes, disintegrators, coating agents, etc.

The daily dose of the preparation can be appropriately determined and is not particularly limited. Preferably, however, the daily dose is such that the total amount of the present compound and β-lactam antibiotic is about 1 to about 200 mg/kg body weight for oral administration and about 1 to about 100 mg/kg body weight for parenteral administration.

The penicillin derivatives of the present invention having the formula (I) can be prepared by the processes shown in the reaction scheme given below.

Reaction Scheme

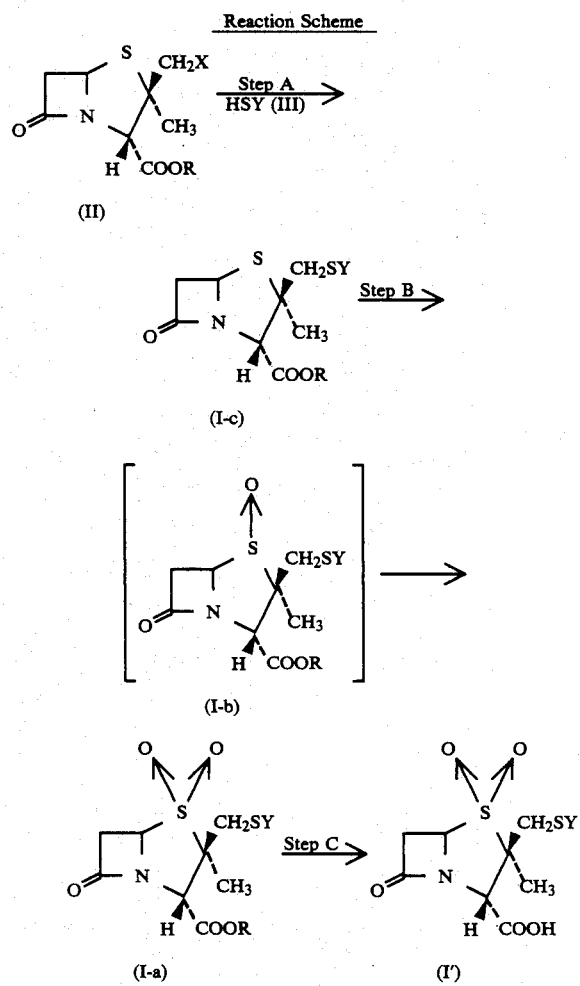

In the above formulas, X is a chlorine or bromine atom; Y is as defined hereinbefore; and R is a penicillin carboxyl ester-forming group.

The steps mentioned in the above reaction scheme are described below.

Step A

A pencillin derivative of the formula (II) is reacted with a mercapto derivative of the formula (III) or a salt thereof to give a compound of the formula (I-c). Per mole of a known penicillin derivative of the formula (II) (Japanese Unexamined Patent Publication (Kokai) No. 58-4788), about 1 to 10 moles, preferably about 1 to 5 moles, of a mercapto derivative (III) or a salt thereof may be used. The reaction is carried out in an appropriate solvent in the presence of a base. Preferable examples of the mercapto derivative (III) which are usable include (a) thiocyanic acid, (b) lower ($C_{2-6}$) aliphatic thiocarboxylic acids such as thioacetic acid, thiopropionic acid, thiobutyric acid, thiopentanoic acid and thiohexanoic acid, (c) mono- or di-lower ($C_{1-6}$) alkyldithiocarbamic acids such as N-methyldithiocarbamic acid, N,N-dimethyldithiocarbamic acid, N-ethyldithiocarbamic acid, N,N-diethyldithiocarbamic acid and N-propyldithiocarbamic acid and (d) unsubstituted or substitued mercaptotetrazole, mercaptobenzothiazole and mercaptothiadiazole, the substituent being lower ($C_{1-6}$) alkyl, phenyl, substituted phenyl having at least one substituent selected from the group consisting of lower ($C_{1-6}$) alkyl, lower ($C_{1-6}$) alkoxy and halogen or the group $-(CH_2)_m-OR_2$ or $-(CH_2)_m-COOR_2$ wherein m and $R_2$ are as defined above, such as 5-mercaptotetrazole, 5-mercapto-1-methyltetrazole, 5-mercapto-1-phenyltetrazole, 5-mercapto-1-(p-chlorophenyl)tetrazole, 2-mercaptobenzothiazole, 2-mercapto-5-methyl-1,3,4-thiadiazole, 5-mercapto-1-(p-methoxyphenyl)tetrazole, 5-mercapto-1-(2'-(α-tetrahydropyranoxy)ethyl)tetrazole, 5-mercaptotetrazole-1-acetic acid, 5-mercapto-1-(2'-hydroxyethyl)tetrazole, 2-mercapto-5-phenyl-1,3,4-thiadiazole, etc. The salt of such mercapto derivative (III) includes alkali metal salts such as potassium salt and sodium salt. The mercapto derivatives (III) mentioned above, inclusive of such salts as mentioned above, are known and can be produced with ease by known methods.

As the base, there may be mentioned inorganic bases such as sodium hydrogen carbonate, potassium hydrogen carbonate, sodium carbonate and potassium carbonate, and organic amines such as pyridine, triethylamine and diisopropylethylamine.

The solvent may be any solvent that does not interfere with the reaction. Thus, for example, various organic solvents such as dimethylformamide, acetone, tetrahydrofuran, dioxane, methanol and ethanol can be used either alone or in the form of a mixture of two or more of them. Mixed solvents composed of such organic solvents and water can also be used. Generally, the reaction proceeds at a temperature of about 0° C. to about 60° C. After the reaction, the desired product may be subjected to the next reaction step without resort to any particular step for the isolation thereof. If desired or necessary, said product can be isolated and purified by using various methods generally known for that purpose either singly or in combination.

Step B

The compound of the formula (I-c) as obtained in the above step A is oxidized to give, via the intermediate sulfoxide of the formula (I-b), the dioxide of the formula (I-a). The oxidation reaction is conducted using an ordinary oxidizing agent such as permanganic acid, periodic acid, peracetic acid, trifluoroperacetic acid, perbenzoic acid, m-chloroperbenzoic acid or hydrogen peroxide. Generally, the oxidizing agent is suitably used in an amount of about 1 to 4 moles per mole of the compound of the formula (I-c), although it may be used in large excess. The sulfoxide of the formula (I-b) can be obtained by suitably selecting the reaction conditions and the number of moles of the oxidizing agent. Said reaction is generally carried out in an appropriate solvent.

Those solvents which do not interfere with the reaction, such as chloroform, pyridine, tetrahydrofuran, dioxane, acetone, methylene chloride, carbon tetrachloride, acetic acid, formic acid, dimethylformamide and water, can all be used. The reaction temperature is not critical. Generally, however, the reaction is carried out at around room temperature or under cooling, for example at a temperature of about 0° C. to 35° C.

The compounds of the formulas (I-c), (I-b) and (I-a) which are obtainable by the above steps A and B may be the esters of the penicillin derivative (I) which are hydrolyzable in vivo according to the type of penicillin carboxyl ester-forming group R but it is generally preferable that such compounds are subsequently subjected to deesterification as shown in Step C to give dioxide derivatives of the formula (I') which, if necessary, are further converted in a conventional manner to pharmaceutically acceptable salts or to esters which are hydrolyzable in vivo. The above compounds of the formulas (I-a), (I-b) and (I-c) may also be directly subjected to ester interchange reaction to give esters which are hydrolyzable in vivo or converted to pharmaceutically acceptable salts in the conventional manner.

Step C

The compound of the formula I-a, either after isolation from the reaction mixture in Step B or without isolation, can be subjected to deesterification reaction to give a penicillin derivative of the formula (I').

The deesterification reaction can be carried out by any known method for conversion of a protected carboxyl group to a free carboxyl group, such as reduction, hydrolysis and so on. Particularly when the penicillin carboxyl ester-forming group R is trichloroethyl, benzyl, p-nitrobenzyl, diphenylmethyl or the like, reduction methods can be advantageously employed. When said group R is 4-methoxybenzyl, tert-butyl, trityl, diphenylmethyl, methoxymethyl, tetrahydropyranyl or the like, methods employing an acid can be employed with advantage.

Among the reduction methods is a method employing a metal such as zinc, amalgamated zinc or the like and/or a chromium salt such as chromium chloride, chromium acetate or the like and an acid such as formic acid, acetic acid or the like. Catalytic reduction is another representative method in this category. For catalytic reduction, the catalyst may for example be platinum, platinum oxide, palladium, palladium oxide, palladium-on-barium sulfate, palladium-on-calcium carbonate, palladium-on-carbon, nickel oxide or Raney nickel. The solvent may be virtually any solvent that does not interfere with the reaction. Preferred solvents are alcohols such as methanol, ethanol, etc., ethers such as tetrahydrofuran, dioxane, etc., esters such as ethyl acetate, fatty acids such as acetic acid, etc., and mixtures of such organic solvents with water.

Referring to the methods using an acid, the acid includes lower fatty acids such as formic acid, acetic acid, etc., trihaloacetic acids such as trichloroacetic acid, etc., hydrohalogenic acids such as hydrochloric acid, hydrofluoric acid, etc., organic sulfonic acids such as p-toluenesulfonic acid, trifluoromethanesulfonic acid, etc., and various mixtures of said acids. The above reaction using an acid does not require a solvent when the acid is liquid but it can be conducted in the presence of a solvent which does not adversely affect the reaction, such as dimethylformamide, dichloromethane, chloroform, tetrahydrofuran, acetone and so on.

The penicillin derivative of the formula (I') according to the present invention, which is a free carboxylic acid, can be converted to a pharmaceutically acceptable salt and/or ester by the salt-forming reaction and/or esterification reaction which is conventional in this field of art.

When the penicillin carboxyl ester-forming group is 3-phthalidyl, 4-crotonolactonyl, γ-butyrolacton-4-yl or the like, the penicillin derivative of the formula (I') can be esterified with a 3-halophthalide, 4-halocrotonolactone, 4-halo-γ-butyrolactone or the like. The halogens of said halo-compounds may generally be chlorine, bromine and iodine. This reaction is carried out by dissolving a salt of the penicillin derivative of the formula (I') in a suitable polar organic solvent such as N,N-dimethylformamide and adding an approximately equimolar amount of the halo-compound to the solution. The reaction temperature is generally in the range of about 0° to 100° C. and perferably about 15° to 35° C. While this esterification reaction can be conducted directly after the deesterification reaction, the free carboxylic acid can be made into a salt once in order to conduct the esterification reaction with greater advantage. As examples of the salt of the penicillin derivative, there may be mentioned salts of alkali metals such as sodium, potassium, etc. and salts of tertiary amines such as triethylamine, ethyldiisopropylamine, N-ethylpiperidine, N,N-dimethylaniline, N-methylmorpholine and so on. After completion of the reaction, the desired compound can be easily isolated by the technique known per se.

The various compounds, penicillin derivatives and pharmaceutically acceptable salts obtained by the above-described respective reaction steps can be isolated at the end of each step and, if necessary, purified by the conventional techniques such as recrystallization, thin layer chromatography, column chromatography and so on.

The following examples further illustrate the present invention.

EXAMPLE 1

Production of p-nitrobenzyl 2α-methyl-2β-thiocyanatomethylpenam-3α-carboxylate (Compound 1)

In a mixture of 3 ml of acetone and 1 ml of water were dissolved 148 mg (0.4 mmole) of p-nitrobenzyl 2β-chloromethyl-2α-methylpenam-3α-carboxylate and 58 mg (0.6 mole) of potassium thiocyanate, and the solution was stirred at 25° C. for 12 hours. The reaction mixture was diluted with 15 ml of ethyl acetate, washed with water and a saturated aqueous solution of sodium chloride twice each, and dried over anhydrous magnesium sulfate. The ethyl acetate layer was concentrated under reduced pressure and the residue was purified by column chromatography to give 149 mg of oil. Yield 95%.

Infrared absorption spectrum (CHCl$_3$): $\nu_{max}$ (cm$^{-1}$)=2150, 1780, 1755.

Nuclear magnetic resonance spectrum (CDCl$_3$): δ (ppm)=1.56 (3H, s), 3.21 (1H, dd), 3.38 (2H, s), 3.67 (1H, dd), 4.80 (1H, s), 5.27 (2H, s), 5.25–5.45 (1H, m), 7.48 (2H, d), 8.15 (2H, d).

EXAMPLE 2

Production of p-methoxybenzyl 2α-methyl-2β-thiocyanatomethylpenam-3α-carboxylate (Compound 2)

In a mixture of 3 ml of acetone and 1 ml of water were dissolved 148 mg (0.4 mmole) of p-methoxybenzyl 2β-chloromethyl-2α-methylpenam-3α-carboxylate and 58 mg (0.6 mmole) of potassium thiocyanate, and the solution was stirred at 25° C. for 22 hours. The reaction mixture was diluted with 20 ml of ethyl acetate, washed with water and a saturated aqueous solution of sodium chloride twice each, and dried over anhydrous magnesium sulfate. The ethyl acetate layer was concentrated under reduced pressure and the residue was purified by column chromatography (silica gel, benzene-ethyl acetate=19:1) to give 150 mg of oil. Yield 94%.

Infrared absorption spectrum (CHCl$_3$):
$\nu_{max}$(cm$^{-1}$)=2150, 1770, 1740, 1610, 1510.

Nuclear magnetic resonance spectrum (CDCl$_3$): δ (ppm)=1.46 (3H, s), 3.03 (1H, dd), 3.31 (2H, s), 3.57 (1H, dd), 3.77 (3H, s), 4.68 (1H, s), 5.11 (2H, s), 5.23-5.40 (1H, m), 6.85 (2H, d), 7.77 (2H, d).

EXAMPLE 3

Production of benzhydryl 2α-methyl-2β-thiocyanatomethylpenam-3α-carboxylate (Compound 3)

In a mixture of 16.1 ml of acetone and 5.4 ml of water were dissolved 862 mg (2.1 mmoles) of benzhydryl 2β-chloromethyl-2α-methylpenam-3α-carboxylate and 313 mg (3.1 mmoles) of potassium thiocyanate and the mixture was stirred at 25° C. for 21 hours. The reaction mixture was diluted with 60 ml of ethyl acetate, washed with water and a saturated aqueous solution of sodium chloride twice each, and dried over anhydrous magnesium sulfate. The ethyl acetate layer was concentrated under reduced pressure and the residue was purified by column chromatography (silica gel, benzene-ethyl acetate=39:1) to give 834 mg of oil. Yield 92%.

Infrared absorption spectrum (CHCl$_3$): $\nu_{max}$ (cm$^{-1}$)=2150, 1775, 1740.

Nuclear magnetic resonance spectrum (CDCl$_3$): δ (ppm)=1.33 (3H, s), 3.00 (1H, dd), 3.28 (2H, s), 3.52 (1H, dd), 4.79 (1H, s), 5.20-5 40 (1H, m), 6.90 (1H, s), 7.10-7.50 (10H, m).

EXAMPLE 4

Production of p-nitrobenzyl 2α-methyl-2β-(1-methyl-5-tetrazolylthio)methylpenam-3α-carboxylate (Compound 4)

In a mixture of 3 ml of acetone and 1 ml of water were dissolved 148 mg (0.4 mmole) of p-nitrobenzyl 2β-chloromethyl-2α-methylpenam-3α-carboxylate, 52 mg (0.45 mmole) of 5-mercapto-1-methyltetrazole and 40 mg (0.4 mmole) of potassium hydrogen carbonate, and the mixture was stirred at 25° C. for 12 hours. The reaction mixture was diluted with 20 ml of ethyl acetate, washed with water and a saturated aqueous solution of sodium chloride twice each, and dried over anhydrous magnesium sulfate.

The ethyl acetate layer was concentrated under reduced pressure and the residue was purified by column chromatography (silica gel, benzene-ethyl acetate=9:1) to give 119 mg of oil. Yield 66%.

Infrared absorption spectrum (CHCl$_3$): $\nu_{max}$ (cm$^{-1}$)=1775, 1755, 1610, 1525 1350.

Nuclear magnetic resonance spectrum (CDCl$_3$): δ (ppm)=1.52 (2H, s), 3.11 (1H, dd), 3.61 (1H, dd), 3.60-4.20 (2H, m), 3.91 (3H, s), 4.81 (1H, s), 5.20-5.45 (1H, m), 5.27 (2H, s), 7.48 (2H, d), 8.15 (2H, d).

EXAMPLE 5

Production of p-nitrobenzyl 2α-methyl-2β-(1-phenyl-5-tetrazolylthio)methylpenam-3α-carboxylate (Compound 5)

In a mixture of 6 ml of acetone and 2 ml of water were dissolved 148 mg (0.4 mmole) of p-nitrobenzyl 2β-chloromethyl-2α-methylpenam-3α-carboxylate, 79 mg (0.44 mmole) of 5-mercapto-1-phenyltetrazole and 40 mg (0.4 mmole) of potassium hydrogen carbonate and the mixture was stirred at 25° C. for 12 hours. The reaction mixture was diluted with 20 ml of ethyl acetate, washed with water and a saturated aqueous solution of sodium chloride twice each, and dried over anhydrous magnesium sulfate.

The ethyl acetate layer was concentrated under reduced pressure and the residue was purified by column chromatography (silica gel, benzene-ethyl acetate=19:1) to give 127 mg of oil. Yield 65%.

Infrared absorption spectrum (CHCl$_3$): $\nu_{max}$ (cm$^{-1}$)=1775, 1750, 1610, 1520, 1350.

Nuclear magnetic resonance spectrum (CDCl$_3$): δ (ppm)=1.52 (3H, s), 3.08 (1H, dd), 3.54 (1H, dd), 3.60-4.20 (2H, m), 4.84 (1H, s), 5.15-5.40 (1H, m), 5.23 (2H, s), 7.15-7.65 (7H, m), 8.12 (2H, d).

EXAMPLE 6

Production of p-nitrobenzyl 2β-(1-p-chlorophenyl-5-tetrazolylthio)methyl-2α-methylpenam-3α-carboxylate (Compound 6)

In a mixture of 75 ml of acetone and 25 ml of water were dissolved 3.70 g of p-nitrobenzyl 2β-chloromethyl-2α-methylpenam-3α-carboxylate, 2.12 g of 5-p-chlorophenyl-5-mercaptotetrazole and 840 mg of sodium hydrogen carbonate and the mixture was stirred at room temperature for 24 hours. The acetone was distilled off under reduced pressure and the residue was extracted with 50 ml of ethyl acetate. The ethyl acetate layer was concentrated to some extent under reduced pressure and the resulting crystals (3.26 g) were collected by filtration. Yield 60%.

Melting point: 168-169° C.

Infrared absorption spectrum (KBr) $\nu_{max}$ (cm$^{-1}$)=1778, 1758.

Nuclear magnetic resonance spectrum (CDCl$_3$): δ (ppm)=1.53 (3H, s), 3.19, 3.60 (1H each, ABX), 3.91, 4.08 (1H each, AB), 4.86 (1H, s), 5.30 (2H, s), 5.30-5.39 (1H, m), 7.56 (4H, s), 7.60 (2H, d), 8.26 (2H, d).

EXAMPLE 7

Production of p-nitrobenzyl 2β-(1-p-methoxyphenyl-5-tetrazolylthio)methyl-2α-methylpenam-3α-carboxylate (Compound 7)

In a mixture of 75 ml of acetone and 25 ml of water were dissolved 3.70 g of p-nitrobenzyl 2β-chloromethyl-2α-methylpenam-3α-carboxylate, 2.08 g of 5-mercapto-1-p-methoxyphenyltetrazole and 840 mg of sodium hydrogen carbonate and the mixture was stirred at room temperature for 18 hours. The acetone was distilled off under reduced pressure and the residue was extracted with 50 ml of ethyl acetate. The ethyl acetate layer was concentrated under reduced pressure and the residue was purified by column chromatography to give 1.52 g of oil. Yield 28%.

Nuclear magnetic resonance spectrum ((CDCl$_3$): δ (ppm)=1.53 (3H, s), 3.19, 5.59 (1H each, ABX), 3.89 (3H, s), 3.89, 4.05 (1H each, AB), 4.85 (1H, s), 5.30 (2H, s), 5.30–5.36 (1H, m), 7.07 (2H, d), 7.45 (2H, d), 7.58 (2H, d), 8.26 (2H, d).

EXAMPLE 8

Production of p-nitrobenzyl 2α-methyl-2β-[1-(2'-(α-tetrahydropyranoxy)ethyl)-5-tetrazolylthio]-methylpenam-3α-carboxylate (Compound 8)

In a mixture of 75 ml of acetone and 25 ml of water were dissolved 3.70 g of p-nitrobenzyl 2β-chloromethyl-2α-methylpenam-3α-carboxylate, 2.30 g of 5-mercapto-1-(2'-(α-tetrahydropyranoxy)ethyl)tetrazole and 840 mg of sodium hydrogen carbonate and the mixture was stirred at room temperature for 24 hours. The acetone was distilled off under reduced pressure and the residue was extracted with 50 ml of methylene chloride. The methylene chloride layer was concentrated under reduced pressure and the residue was purified by column chromatography to give 1.15 g of oil. Yield 20%.

Infrared absorption spectrum (CHCl$_3$): $\nu_{max}$ (cm$^{-1}$)=1785, 1760.

Nuclear magnetic resonance spectrum ((CDCl$_3$): δ (ppm)=1.55 (3H, s), 1.26–1.80 (6H, m), 3.05–4.55 (11H, m), 4.83 (1H, s), 5.30 (2H, s), 5.30–5.37 (1H, m), 7.59 (2H, d), 8.26 (2H, d).

EXAMPLE 9

Production of p-nitrobenzyl 2β-(1-diphenylmethoxycarbonylmethyl-5-tetrazolylthio)-methyl-2α-methylpenam-3α-carboxylate (Compound 9)

In a mixture of 54 ml of acetone and 18 ml of water were dissolved 7.42 g of p-nitrobenzyl 2β-chloromethyl-2α-methylpenam-3α-carboxylate, 3.20 g of 5-mercaptotetrazole-1-acetic acid and 4.0 g of sodium hydrogen carbonate and the mixture was stirred at room temperature for 15 hours. The acetone was distilled off and the residue was extracted with 200 ml of ethyl acetate. The ethyl acetate layer was concentrated under reduced pressure and the residue was dissolved in 50 ml of methylene chloride.

Under ice-cooling, 2.83 g of diphenyldiazomethane was added thereto and the mixture was stirred at room temperature for 1 hour. The methylene chloride was distilled off under reduced pressure and the residue was purified by silica gel column chromatography to give 1.85 g of oil. Yield 14%.

Nuclear magnetic resonance spectrum ((CDCl$_3$): δ (ppm)=1.47 (3H, s), 3.13, 3.57 (1H each, ABX), 3.78, 3.90 (1H each, AB), 4.77 (1H, s), 5.17 (2H, s), 5.27 (2H, s), 5.27–5.35 (1H, m), 6.94 (1H, s), 7.31 (10H, s), 7.55 (2H, d), 8.25 (2H, d).

EXAMPLE 10

Production of p-nitrobenzyl 2α-methyl-2β-(2-benzothiazolylthio)methylpenam-3α-carboxylate (Compound 10)

In a mixture of 3 ml of acetone and 1 ml of water were dissolved 74 mg (0.2 mmole) of p-nitrobenzyl 2β-chloromethyl-2α-methylpenam-3α-carboxylate, 35 mg (0.21 mmole) of 2-mercaptobenzothiazole and 20 mg (0.2 mmole) of potassium hydrogen carbonate and the mixture was stirred at 25° C. for 30 hours. The reaction mixture was diluted with 10 ml of ethyl acetate and washed with water and a saturated aqueous solution of sodium chloride twice each and dried over anhydrous magnesium sulfate. The ethyl acetate layer was concentrated under reduced pressure and the residue was purified by column chromatography (silica gel, benzene-ethyl acetate=19:1) to give 36 mg of p-nitrobenzyl 2α-methyl-2β-(2-benzothiazolylthio)methylpenam-3αcarboxylate. Yield 35%.

Infrared absorption spectrum (CHCl$_3$): $\nu_{max}$ (cm$^{-1}$)=1775, 1610, 1525.

Nuclear magnetic resonance spectrum ((CDCl$_3$): δ (ppm)=1.53 (3H, s), 3.12 (1H, dd), 3.58 (1H, dd), 3.70–4.25 (2H, m), 4.91 (1H, s), 5.20–5.40 (1H, m), 5.22 (2H, s), 7.10–7.90 (5H, m), 8.11(2H, d).

EXAMPLE 11

Production of p-nitrobenzyl 2α-methyl-2β-(5-methyl-2-(1,3,4-thiadiazolyl)thio)methylpenam-3α-carboxylate (Compound 11)

In a mixture of 6 ml of acetone and 2 ml of water were dissolved 148 mg (0.4 mmole) of p-nitrobenzyl 2β-chloromethyl-2α-methylpenam-3α-carboxylate, 56 mg (0.42 mmole) of 2-mercapto-5-methyl-1,3,4-thiadiazole and 40 mg (0.4 mmole) of potassium hydrogen carbonate and the mixture was stirred at 25° C. for 24 hours. The reaction mixture was diluted with 20 ml of ethyl acetate and washed with water and a saturated aqueous solution of sodium chloride twice each and dried over anhydrous magnesium sulfate. The ethyl acetate layer was concentrated under reduced pressure and the residue was purified by column chromatography (silica gel, benzene-ethyl acetate=19:1) to give 68 mg of p-nitrobenzyl 2α-methyl-2β-(5-methyl-2-(1,3,4-thiadiazolyl)thio)methylpenam-3α-carboxylate. Yield 37%.

Infrared absorption spectrum (CHCl$_3$): $\nu_{max}$ (cm$^{-1}$)=1775, 1610, 1525.

Nuclear magnetic resonance spectrum (CDCl$_3$): δ (ppm)=1.51 (3H, s), 2.69 (3H, s), 3.10 (1H, dd), 3.59 (1H, dd), 3.60–4.20 (2H, m), 4.83 (1H, s), 5.20–5.40 (1H, m), 5.24 (2H, s), 7.49 (2H, d), 8.15 (2H, d).

EXAMPLE 12

Production of p-nitrobenzyl 2α-methyl-2β-dimethylthiocarbamoylthiomethylpenam-3α-carboxylate (Compound 12)

In a mixture of 6 ml of acetone and 2 ml of water were dissolved 148 mg (0.4 mmole) of p-nitrobenzyl 2β-chloromethyl-2α-methylpenam-3α-carboxylate and 61 mg (0.44 mmole) of sodium N,N-dimethyldithiocarbamate and the mixture was stirred at 25° C. for 12 hours. The reaction mixture was diluted with 15 ml of ethyl acetate and washed with water and a saturated aqueous solution of sodium chloride twice each and dried over anhydrous magnesium sulfate. The ethyl acetate layer was concentrated under reduced pressure and the residue was purified by column chromatography to give 24 mg of oil.

Infrared absorption spectrum (CHCl$_3$): $\nu_{max}$ (cm$^{-1}$)=1775, 1745 (Sh).

Nuclear magnetic resonance spectrum ((CDCl$_3$): δ (ppm)=1.51 (3H, s), 3.15 (1H, dd), 3.30–3.75 (9H, m), 4.79 (1H, s), 5.15–5.30 (1H, m), 5.23 (2H, s), 7.55 (2H, d), 8.20 (2H, d).

EXAMPLE 13

Production of p-nitrobenzyl
2α-methyl-2β-acetylthiomethylpenam-3α-carboxylate
(Compound 13)

In a mixture of 3 ml of acetone and 1 ml of water were dissolved 148 mg (0.4 mmole) of p-nitrobenzyl 2β-chloromethyl-2α-methylpenam-3α-carboxylate, 34 mg (0.45 mmole) of thioacetic acid and 40 mg (0.4 mmole) of potassium hydrogen carbonate and the mixture was stirred at 25° C. for 12 hours. The reaction mixture was diluted with 20 ml of ethyl acetate, washed with water and a saturated aqueous solution of sodium chloride twice each, and dried over anhydrous magnesium sulfate. The ethyl acetate layer was concentrated under reduced pressure and the residue was purified by column chromatography to give 27 mg of oil.

Infrared absorption spectrum (CHCl$_3$): $\nu_{max}$ (cm$^{-1}$)=1780, 1700.

Nuclear magnetic resonance spectrum ((CDCl$_3$): δ (ppm)=1.42 (3H, s), 2.38 (3H, s), 3.14 (1H, dd), 3.10-3.65 (2H, m), 3.59 (1H, dd), 4.67 (1H, s), 5.20-5.45 (1H, m), 5.27 (2H, s), 7.53 (2H, d), 8.21 (2H, d).

EXAMPLE 14

Production of p-nitrobenzyl
2α-methyl-2β-thiocyanatomethylpenam-3α-carboxylate 1-oxide (Compound 14)

In 20 ml of dichloromethane was dissolved 431 mg (2.0 mmoles) of p-nitrobenzyl 2α-methyl-2β-thiocyanatometylpenam-3α-carboxylate, and under ice cooling and stirring, a solution of 41 mg (2.0 mmoles) of m-chloroperbenzoic acid (80%) in 10 ml of dichloromethane was added dropwise. The mixture was stirred at room temperature for 2 hours. The reaction mixture was then washed with an aqueous solution of sodium hydrogen sulfite, an aqueous solution of sodium hydrogen carbonate and a saturated aqueous solution of sodium chloride twice each, and dried over anhydrous magnesium sulfate. The dichloromethane solution was concentrated under reduced pressure and the residue was purified by column chromatography (silica gel, acetone-chloroform=19:1) to give 772 mg of oil. Yield 94%.

Infrared absoprtion spectrum (CHCl$_3$): $\nu_{max}$ (cm$^{-1}$)=2150, 1790, 1755.

Nuclear magnetic resonance spectrum ((CDCl$_3$): δ (ppm)=1.41 (3H, s), 3.30-3.65 (2H, m), 3.70 (2H, s), 4.67 (1H, s), 5.04 (1H, t), 5.34 (2H, s), 7.57 (2H, d), 8.25 (2H, d).

EXAMPLE 15

Production of p-methoxybenzyl
2α-methyl-2β-thiocyanatomethylpenam-3α-carboxylate 1-oxide (Compound 15)

In 10 ml of dichloromethane was dissolved 592 mg (1.56 mmoles) of p-methoxybenzyl 2α-methyl-2β-thiocyanatomethylpenam-3α-carboxylate and under ice-cooling and stirring, a solution of 354 mg (1.64 mmoles) of m-chloroperbenzoic acid (80%) in 10 ml of dichloromethane was added dropwise. The mixture was stirred at room temperature for 2 hours. The reaction mixture was washed with an aqueous solution of sodium hydrogen sulfite, an aqueous solution of sodium hydrogen carbonate and a saturated aqueous solution of sodium chloride and, then, dried over anhydrous magnesium sulfate. The dichloromethane solution was concentrated under reduced pressure and the residue was purified by column chromatography (silica gel, acetone-chloroform=19:1) to give 479 mg of oil. Yield 78%.

Infrared absorption spectrum (CHCl$_3$): $\nu_{max}$ (cm$^{-1}$)=2150, 1790, 1755.

Nuclear magnetic resonance spectrum (CDCl$_3$): δ (ppm)=1.25 (3H, s), 3.21 (2H, d), 3.60 (2H, s), 3.78 (3H, s), 4.54 (1H, s), 4.94 (1H, t), 5.0-5.4 (2H, m), 6.91 (2H, d), 7.83 (2H, d).

EXAMPLE 16

Benzhydryl
2α-methyl-2β-thiocyanatomethylpenam-3α-carboxylate 1-oxide (Compound 16)

In 10 ml of dichloromethane was dissolved 742 mg (1.75 mmoles) of benzhydryl 2α-methyl-2β-thiocyanatomethylpenam-3α-carboxylate and under ice-cooling and stirring, a solution of 397 mg (1.84 mmoles) of m-chloroperbenzoic acid (80%) in 10 ml of dichloromethane was added dropwise. The mixture was stirred at room temperature for 2 hours. The reaction mixture was washed with an aqueous solution of sodium hydrogen sulfite, an aqueous solution of sodium hydrogen carbonate and a saturated aqueous solution of sodium chloride twice each, and dried over anhydrous magnesium sulfate. The dichloromethane solution was concentrated under reduced pressure and the residue was purified by column chromatography (silica gel, acetone-chloroform=49:1) to give 669 mg of oil. Yield 87%.

Infrared absorption spectrum (CHCl$_3$): $\nu_{max}$ (cm$^{-1}$)=2160, 1795, 1755.

Nuclear magnetic resonance spectrum (CDCl$_3$): δ (ppm)=1.11 (3H,s), 3.29 (2H, d), 3.61 (2H, s), 4.63 (1H, s), 4.87 (1H, t), 6.94 (1H, s), 7.1-7.5 (10H, m).

EXAMPLE 17

Production of p-nitrobenzyl
2β-(1-p-chlorophenyl-5-tetrazolylthio)methyl-2α-methylpenam-3α-carboxylate 1-oxide (Compound 17)

To a solution of 273 mg of p-nitrobenzyl 2β-(1-p-chlorophenyl-5-tetrazolylthio)methyl-2α-methylpnam-3α-carboxylate in 3 ml of methylene chloride were added 46 mg of formic acid and 0.1 ml of a 30% aqueous solution of hydrogen peroxide and the mixture was stirred at room temperature for 5 hours. Then, 5 ml of water was added thereto and the methylene chloride layer was separated and concentrated under reduced pressure. The residue was purified by column chromatography to give 269 mg of oil. Yield 96%.

Infrared absorption spectrum (CHCl$_3$): $\nu_{max}$ (cm$^{-1}$)=1792, 1760.

Nuclear magnetic resonance spectrum (CDCl$_3$): δ (ppm)=1.31 (3H, s), 3.39-3.43 (2H, m), 4.04, 4.49 (1H each, AB), 4.73 (1H, s), 4.94-5.02 (1H, m), 5.34, 5.44 (1H each, AB), 7.56 (4H, s), 7.76 (2H, d), 8.31 (2H, d).

EXAMPLE 18

Production of p-nitrobenzyl
2α-methyl-2β-thiocyanatomethylpenam-3α-carboxylate 1,1-dioxide (Compound 18)

In a mixture of 5.5 ml of glacial acetic acid and 0.9 ml of water was dissolved 145 mg (0.37 mmole) of p-nitrobenzyl 2α-methyl-2β-thiocyanatomethylpenam-3α-carboxylate, and with stirring at room temperature, 70 mg (0.44 mmole) of potassium permanganate was added gradually thereto over 30 minutes. The mixture was stirred at room temperature for 4 hours. Then, 34.5% hydrogen peroxide was added thereto until the color of the mixture disappeared, after which water was added. The mixture was then extracted with chloroform and the chloroform layer was washed with an aqueous solution of sodium hydrogen carbonate and dried over anhydrous magnesium sulfate. The chloroform layer was concentrated under reduced pressure to give 154 mg of p-nitrobenzyl 2α-methyl-2β-thiocyanatomethylpenam-3α-carboxylate 1,1-dioxide. Yield 98%. Melting point 149°–150° C.

Infrared absorption spectrum (CHCl₃): $v_{max}$ (cm$^{-1}$)=2150, 1790, 1755, 1725.

Nuclear magnetic resonance spectrum (CDCl₃): δ (ppm)=1.58 (s, 3H), 3.30–3.70 (m, 2H,), 3.63 (s, 2H), 4.60–4.80 (m, 1H), 4.72 (s, 1H), 5.33 (s, 2H), 7.53 (d, 2H), 8.18 (d, 2H).

EXAMPLE 19

Production of p-nitrobenzyl 2α-methyl-2β-(1-methyl-5-tetrazolylthio)methylpenam-3α-carboxylate 1,1-dioxide (compound 19)

In a mixture of 3.2 ml of glacial acetic acid and 0.5 ml of water was dissolved 138 mg (0.31 mmole) of p-nitrobenzyl 2α-methyl-2β-(1-methyl-5-tetrazolylthio)methylpenam-3α-carboxylate, and with stirring at room temperature, 58 mg (0.37 mmole) of potassium permanganate was added gradually thereto over 30 minutes. The mixture was further stirred at room temperature for 4 hours. Then, an aqueous solution of hydrogen peroxide was added thereto until the color of the mixture disappeared, after which 5 ml of water was added, followed by extraction with chloroform. The chloroform layer was washed with an aqueous solution of sodium hydrogen carbonate and a saturated aqueous solution of sodium chloride and dried over anhydrous magnesium sulfate. The chloroform layer was concentrated under reduced pressure to give 138 mg of oil. Yield 93%.

Infrared absorption spectrum (CHCl₃): $v_{max}$ (cm$^{-1}$)=1805, 1760, 1605.

Nuclear magnetic resonance spectrum (CDCl₃): δ (ppm)=1.48 (3H, s), 3.30–3.70 (2H, m), 3.80–4.55 (2H, m), 4.55–4.90 (1H, m), 3.94 (3H, s), 4.75 (1H, s), 5.33 (2H, s), 7.63 (2H, d), 8.20 (2H, d).

EXAMPLE 20

Production of p-nitrobenzyl 2α-methyl-2β-(1-phenyl-5-tetrazolylthio)methylpenam-3α-carboxylate 1,1-dioxide (Compound 20)

In a mixture of 13.4 ml of glacial acetic acid and 2,1 ml of water was dissolved 657 mg (1.34 mmoles) of p-nitrobenzyl 2α-methyl-2β-(1-phenyl-5-tetrazolylthio)methylpenam-3α-carboxylate, and with stirring at room temperature, 58 mg (1.61 mmoles) of potassium permanganate was added gradually thereto over 30 minutes. The mixture was further stirred at room temperature for 4 hours. Then, an aqueous solution of hydrogen peroxide was added thereto until the color of the mixture disappeared, after which the solution was diluted with water and extracted with chloroform.

The chloroform layer was washed with water, an aqueous solution of sodium hydrogen carbonate and a saturated aqueous solution of sodium chloride in that order and dried over anhydrous magnesium sulfate. The chloroform layer was concentrated under reduced pressure to give 644 mg of p-nitrobenzyl 2α-methyl-2β-(1-phenyl-5-tetrazolylthio)methylpenam-3α-carboxylate 1,1-dioxide. Yield 92%. Melting point 151°–153° C.

Infrared absorption spectrum (KBr): $v_{max}$ (cm$^{-1}$)=1805, 1765, 1610, 1600, 1530.

Nuclear magnetic resonance spectrum ((CDCl₃): δ (ppm)=1.52 (3H, s), 3.35–3.60 (2H, m), 3.80–4.55 (2H, m), 4.50–4.70 (1H, m), 4.74 (1H, s), 5.31 (2H, s), 7.48 (5H, s), 7.61 (2H, d), 8.18 (2H, d).

EXAMPLE 21

Production of p-nitrobenzyl 2β-(1-p-chlorophenyl-5-tetrazolylthio)methyl-2α-methylpenam-3α-carboxylate 1,1-dioxide (Compound 21)

In a mixture of 28 ml of glacial acetic acid and 5 ml of water was dissolved p-nitrobenzyl 2β-(1-p-chlorophenyl-5-tetrazolylthio)methyl-2α-methylpenam-3α-carboxylate, and with ice-cooling and stirring, 520 mg of potassium permanganate was gradually added thereto. The mixture was stirred at the same temperature for 1.5 hours and further at room temperature for 2.5 hours. Then, a 30% aqueous solution of hydrogen peroxide was added until the color of the mixture disappeared and the resulting precipitate was collected by filtration. Recrystallization from methanol-water gave 0.58 g of crystals. Yield 36%.

Melting point: 146°–147° C.

Infrared absorption spectrum (KBr): $v_{max}$ (cm$^{-1}$)=1818, 1800, 1752.

Nuclear magnetic resonance spectrum (CDCl₃): δ (ppm)=1.53 (3H, s), 3.51–3.56 (2H, m), 4.08, 4.37 (1H each, AB), 4.62–4.67 (1H, m), 4.77 (1H, s), 5.38 (2H, s), 7.55 (4H, s), 7.73 (2H, d), 8.30 (2H, d).

EXAMPLE 22

Production of p-nitrobenzyl 2β-(1-p-methoxyphenyl-5-tetrazolylthio)methyl-2α-methylpenam-3α-carboxylate 1,1-dioxide (Compound 22)

In a mixture of 28 ml of glacial acetic acid and 5 ml of water was dissolved 1.50 g of p-nitrobenzyl 2β-(1-p-methoxyphenyl-5-tetrazolylthio)methyl-2α-methylpenam-3α-carboxylate, and with ice-cooling and stirring, 520 mg of potassium permanganate was gradually added. The mixture was stirred at the same temperature for 2.5 hours and further at room temperature for 2.0 hours. Then, a 30% aqueous solution of hydrogen peroxide was added thereto until the color of the mixture disappeared, followed by filtration to collect crystals. Recrystallization from methanol-water gave 1.23 g of crystals. Yield 77%.

Melting point: 142°–144° C.

Infrared absorption spectrum (KBr): $v_{max}$ (cm$^{-1}$)=1798, 1750.

Nuclear magnetic resonance spectrum (CDCl₃): δ (ppm)=1.53 (3H, s), 3.51–3.55 (2H, m), 3.89 (3H, s), 4.05, 4.36 (1H each, AB), 4.62–4.69 (1H, m), 4.77 (1H, s), 5.37 (2H, s), 7.05 (2H, d), 7.45 (2H, d), 7.73 (2H, d), 8.30 (2H, d).

EXAMPLE 23

Production of p-nitrobenzyl
2α-methyl-2β-[1-(2'-(α-tetrahydropyranoxy)ethyl)-5-tetrazolylthio]methylpenam-3α-carboxylate 1,1-dioxide (Compound 23)

In a mixture of 30 ml of acetone and 3 ml of water was dissolved 1.15 g of p-nitrobenzyl 2α-methyl-2β-[1-(2'-(α-tetrahydropyranoxy)ethyl)-5-tetrazolylthio]methylpenam-3α-carboxylate, followed by addition of 370 mg of glacial acetic acid. Then, with ice-cooling and stirring, 810 mg of potassium permanganate was added gradually and the mixture was stirred at the same temperature for 4 hours and further at room temperature for 1 hour. Thereafter, the precipitated manganese dioxide was filtered off and the filtrate was extracted with 30 ml of methylene chloride. The methylene chloride layer was concentrated under reduced pressure and the residue was purified by silica gel column chromatography to give 720 mg of oil. Yield 60%.

Nuclear magnetic resonance spectrum (CDCl$_3$): δ (ppm)=1.47 (3H, s), 1.26–1.80 (6H, m), 3.40–3.60 (2H, m), 3.72–4.69 (10H, m), 4.74 (1H, s), 5.36 (2H, s), 7.71 (2H, d), 8.27 (2H, d).

EXAMPLE 24

Production of p-nitrobenzyl
2β-[1-(2'-hydoxyethyl)-5-tetrazolylthio]methyl-2α-methylpenam-3α-carboxylate 1,1-dioxide (Compound 24)

In a mixture of 15 ml of methanol and 5 ml of methylene chloride were dissolved 720 mg of p-nitrobenzyl 2α-methyl-2β-[1-(2'-(α-tetrahydropyranoxy)ethyl)-5-tetrazolylthio]methylpenam-3α-carboxylate 1,1-dioxide and 229 mg of p-toluensulfonic acid monohydrate and the mixture was stirred at room temperature for 6 hours. The solvent was distilled off under reduced pressure and the residue was purified by silica gel column chromatography to give 291 mg of oil. Yield 47%.

Nuclear magnetic resonance spectrum (CDCl$_3$): δ (ppm)=1.44 (3H, s), 2.38 (1H, t, disappeared upon addition of D$_2$O) 3.52–3.56 (2H, m), 4.09–4.18 (4H, m), 4.36–4.45 (2H, m), 4.61–4.68 (1H, m), 4.87 (1H, s), 5.32 (2H, s), 7.67 (2H, d), 8.28 (2H, d).

EXAMPLE 25

Production of p-nitrobenzyl
2β-(1-diphenylmethoxycarbonylmethyl-5-tetrazolylthio)methyl-2α-methylpenam-3α-carboxylate 1,1-dioxide (Compound 25)

In a mixture of 18 ml of glacial acetic acid and 3 ml of water was dissolved 1.85 g of p-nitrobenzyl 2β-(1-diphenylmethoxycarbonylmethyl-5-tetrazolylthio)-methyl-2α-methylpenam-3α-carboxylate. Then, with ice-cooling and stirring, 530 mg of potassium permanganate was added gradually and the mixture was stirred at the same temperature for 2.5 hours and further at room temperature for 2 hours. Then, a 30% aqueous solution of hydrogen peroxide was added until the color of the reaction mixture disappeared, followed by extraction with 30 ml of ethyl acetate. Then, the ethyl acetate was distilled off under reduced pressure and the residue was purified by column chromatography to give 740 mg of oil. Yield 38%.

Infrared absorption spectrum (CHCl$_3$): ν$_{max}$ (cm$^{-1}$)=1818, 1762.

Nuclear magnetic resonance spectrum (CDCl$_3$): δ (ppm)=1.41 (3H, s), 3.50–3.54 (2H, m), 3.93, 4.17 (1H each, AB), 4.56–4.66 (1H, m), 4.67 (1H, s), 5.18 (2H, s), 5.31 (2H, s), 6.94 (1H, s), 7.32 (10H, s), 7.64 (2H, d), 8.26 (2H, d).

EXAMPLE 26

Production of sodium
2α-methyl-2β-thiocyanatomethylpenam-3α-carboxylate 1,1-dioxide (Compound 26)

In a mixture of 5.5 ml of ethyl acetate and 3.5 ml of water and in the presence of 60 mg of sodium hydrogen carbonate, low-pressure catalytic hydrogenation of 300 mg of p-nitrobenzyl 2α-methyl-2β-thiocyanatomethylpenam-3α-carboxylate 1,1-dioxide was conducted using 60 mg of 10% palladium-on-carbon at room temperature. After hydrogen ceased to be absorbed, the reaction mixture was filtered and the aqueous layer was separated and subjected to column chromatography on MCI gel (CHP-20P, Mitsubishi Chemical Industries Ltd.). The eluate was lyophilized to give 13 mg of pale yellow powder.

Melting point: 140°–150° C. (decomposition)

Infrared absorption spectrum (KBr): ν$_{max}$ (cm$^{-1}$)=2152, 1780, 1622.

Nuclear magnetic resonance spectrum (D$_2$O): δ (ppm)=1.69 (3H, s), 3.34–3.80 (2H, m), 392 (2H, s), 4.42 (1H, s), 5.05–5.11 (1H, m).

EXAMPLE 27

Production of sodium
2α-methyl-2β-(1-methyl-5-tetrazolyl)thiomethylpenam-3α-carboxylate 1,1-dioxide (Compound 27)

In a mixture of 9 ml of ethyl acetate and 6 ml of water and in the presence of 103 mg of sodium hydrogen carbonate, low-pressure catalytic hydrogenation of 590 mg of p-nitrobenzyl 2α-methyl-2β-(1-methyl-5-tetrazolyl)thiomethylpenam-3α-carboxylate 1,1-dioxide was conducted using 118 mg of 10% palladium-on-carbon at room temperature. When hydrogen ceased to be absorbed, the reaction mixture was filtered and the aqueous layer was separated and subjected to column chromatography on MCI gel (CHP-20P, Mitsubishi Chemical Industries Ltd.). The eluate was lyophilized to give 183 mg of pale yellow powder.

Melting point: 157°–158° C. (decomposition)

Infrared absorption spectrum (KBr): ν$_{max}$ (cm$^{-1}$)=1785, 1628.

Nuclear magnetic resonance spectrum (D$_2$O): δ (ppm)=1.62 (3H, s), 3.39 (1H, dd), 3.67 (1H, dd), 4.06 (3H, s), 4.10–4.11 (2H, m), 4.47 (1H, s), 4.99–5.05 (1H, m).

EXAMPLE 28

Production of sodium
2α-methyl-2β-(1-phenyl-5-tetrazolyl)thiomethylpenam-3α-carboxylate 1,1-dioxide (Compound 28)

In a mixture of 3.5 ml of ethyl acetate and 2.5 ml of water and in the presence of 38 mg of sodium hydrogen carbonate, low-pressure catalytic hydrogenation of 245 mg of p-nitrobenzyl 2α-methyl-2β-(1-pheny-5-tetrazolyl)thiomethylpenam-3α-carboxylate 1,1-dioxide was conducted using 50 mg of 10% palladium-on-carbon at room temperature. When hydrogen ceased to be absorbed, the reaction mixture was filtered and the aqueous layer was separated and subjected to column chromatography on MCI gel (CHP-20P, Mitsubishi Chemical Industries Ltd.). The eluate was lyophilized to give 117 mg of pale yellow powder.

Melting point 208°–210° C. (decomposition).

Infrared absorption spectrum (KBr): $\nu_{max}$ (cm$^{-1}$) = 1782, 1620.

Nuclear magnetic resonance spectrum (D$_2$O): δ (ppm) = 1.55 (3H, s), 3.25–3.80 (2H, m), 4.12–4.14 (2H, m), 4.45 (1H, s), 4.96–5.11 (1H, m), 7.67 (5H, s).

EXAMPLE 29

Production of sodium 2β-(1-p-chlorophenyl-5-tetrazolylthio)methyl-2α-methylpenam-3α-carboxylate 1,1-dioxide (Compound 29)

In a mixture of 20 ml of ethyl acetate and 20 ml of water and in the presence of 42 mg of sodium hydrogen carbonate, low-pressure catalytic hydrogenation of 289 mg of p-nitrobenzyl 2β-(1-p-chlorophenyl-5-tetrazolylthio)methyl-2α-methylpenam-3α-carboxylate 1,1-dioxide was conducted using 289 mg of 5% palladium-on-carbon at room temperature. When hydrogen ceased to be absorbed, the reaction mixture was filtered and the aqueous layer was separated and subjected to column chromatography on MCI gel (CHP-20P, Mitsubishi Chemical Industries Ltd.). The eluate was lyophilized to give 183 mg of pale yellow powder. Yield 78%.

Melting point: 172°–173° C. (decomposition).

Infrared absorption spectrum (KBr): $\nu_{max}$ (cm$^{-1}$) = 1790, 1620.

Nuclear magnetic resonance spectrum (D$_2$O): δ (ppm) = 1.55 (3H, s), 3.37, 3.65 (1H each, ABX), 4.07, 4.20 (1H each, AB), 4.44 (1H, s), 4.97–5.02 (1H, m), 7.66 (4H, s).

EXAMPLE 30

Production of sodium 2β-(1-p-methoxyphenyl-5-tetrazolylthio)methyl-2α-methylpenam-3α-carboxylate 1,1-dioxide (Compound 30)

In a mixture of 30 ml of ethyl acetate and 30 ml of water and in the presence of 42 mg of sodium hydrogen carbonate, low-pressure catalytic hydrogenation of 287 mg of p-nitrobenzyl 2β-(1-p-methoxyphenyl-5-tetrazolylthio)methyl-2α-methylpenam-3α-carboxylate 1,1-dioxide was conducted using 228 mg of 5% palladium-on-carbon at room temperature. When hydrogen ceased to be absorbed, the reaction mixture was filtered and the aqueous layer was separated and subjected to column chromatography on MCI gel (CHP-20P, Mitsubishi Chemical Industries Ltd.). The eluate was lyophilized to give 214 mg of pale yellow powder. Yield 92%.

Melting point 165°–167° C. (decomposition).

Infrared absorption spectrum (KBr): $\nu_{max}$ (cm$^{-1}$) = 1802, 1638.

Nuclear magnetic resonance spectrum (D$_2$O): δ (ppm) = 1.54 (3H, s), 3.36, 3.65 (1H each, ABX), 3.93 (3H, s), 4.04, 4.16 (1H each, AB), 4.44 (1H, s), 4.84–5.00 (1H, m), 7.20 (2H, d), 7.57 (2H, d).

EXAMPLE 31

Production of sodium 2β-[1-(2'-hydroxyethyl)-5-tetrazolylthio]methyl-2α-methylpenam-3α-carboxylate 1,1-dioxide (Compound 31)

In a mixture of 20 ml of ethyl acetate and 20 ml of water and in the presence of 48 mg of sodium hydrogen carbonate, low-pressure catalytic hydrogenation of 290 mg of p-nitrobenzyl 2β-[1-(2'-hydroxyethyl)-5-tetrazolylthio]methyl-2α-methylpenam-3α-carboxylate 1,1-dioxide was conducted using 290 mg of 5% palladium-on-carbon at room temperature. When hydrogen ceased to be absorbed, the reaction mixture was filtered and the aqueous layer was separated and subjected to column chromatography on MCI gel (CHP-20P, Mitsubishi Chemical Industries Ltd.). The eluate was lyophilized to give 157 mg of pale yellow powder. Yield 82%.

Infrared absorption spectrum (KBr): $\nu_{max}$ (cm$^{-1}$) = 1780, 1624.

Nuclear magnetic resonance spectrum (D$_2$O): δ (ppm) = 1.61 (3H, s), 3.39, 3.67 (1H each, ABX), 4.01 (2H, t), 4.09, 4.18 (1H each, AB), 4.46 (1H, s), 4.58 (2H, t), 4.99–5.05 (1H, m).

The compounds obtained in some of the foregoing examples were investigated for β-lactamase inhibitory activity and antibacterial activity.

(1) Test for β-lactamase inhibitory activity

The inhibitory activity of each compound against penicillinase (β-lactamase) from Bacillus SP was determined by microiodometry [Tanpakushitsu Kakusan Koso (Proteins, Nucleic Acids and Enzymes), vol. 23, No.5, pp 391–400 (1978)] using penicillin G as a substrate. Table 1 given below shows the results.

TABLE 1

| Compound No. | 50% Inhibitory Concentration (μM) |
|---|---|
| 26 | 9.8 |
| 27 | 0.87 |
| 28 | 1.0 |
| 29 | 0.48 |
| 30 | 0.75 |
| 31 | 1.82 |

(2) Test for antibacterial activity (1) The minimal inhibitory concentrations (MIC) of piperacillin in the presence of 10 μg/ml of compounds of the present invention against various bacteria were determined by the MIC assay method of Japan Society of Chemotherapy (Chemotherapy 29, No. 1, pp. 76–79, 1981). The MIC values of various compounds according to the present invention and of piperacillin, as used singly, were also determined. Each test strain was grown in Mueller Hinton Broth (Difco) and used for inoculation after dilution to a concentration of 10$^6$ CFU/ml. The assay media (Mueller Hinton Broth) containing piperacillin and the compound according to the present invention in a series of concentrations were inoculated with the test strain and incubated at 37° C. for 20 hours. The minimum concentration at which no more than 5 colonies were observed was determined. The results are shown in Table 2. Though not shown, the MIC values of the compounds according to the present invention, as used singly, were invariably not less than 25 μg/ml. All the test strains used in the above assays were β-lactamase producers.

TABLE 2

| Test strain | Piperacillin alone | Piperacillin plus the following compound MIC (μg/ml) | | | | | |
|---|---|---|---|---|---|---|---|
| | | Compound 26 | Compound 27 | Compound 28 | Compound 29 | Compound 30 | Compound 31 |
| *Echerichia coli* SHV 1 | 12.5 | 0.39 | 0.78 | 3.13 | 1.56 | 3.13 | 0.78 |
| *Klebsiella pneumoniae* 101 L (TEM1) | 200 | 0.78 | 1.56 | 25 | 12.5 | 25 | 3.13 |
| *Morganella morganii* 119 | 25 | ≦0.10 | 1.56 | 25 | 25 | 12.5 | 3.13 |
| *Serratia marcescens* 200 L (TEM + C) | 25 | 3.13 | 0.78 | 6.25 | 3.13 | 12.5 | 0.78 |
| *Acinetobacter* 450 L | 200 | 12.5 | 1.56 | 25 | 12.5 | 25 | 12.5 |
| *Pseudomonas aeruginosa* PSE 3 | 50 | 3.13 | 3.13 | 12.5 | 12.5 | 12.5 | 3.13 |
| *Staphylococcus aureus* 54 K | 6.25 | 0.39 | 0.78 | 0.78 | 0.78 | 0.78 | 0.78 |

Given below are examples of preparation of the resent antibacterial compositions.

PREPARATION EXAMPLE 1

| | |
|---|---|
| Ampicillin | 200 mg |
| Compound 31 | 200 mg |
| Lactose | 100 mg |
| Crystalline cellulose | 57 mg |
| Magnesium stearate | 3 mg |
| Total | 560 mg |
| | (amount per capsule) |

The above ingredients are formulated in the proportions listed above into a capsule.

PREPARATION EXAMPLE 2

| | |
|---|---|
| Amoxycillin | 100 mg |
| Compound 29 | 70 mg |
| Lactose | 330 mg |
| Corn starch | 490 mg |
| Hydroxypropylmethylcellulose | 10 mg |
| Total | 1000 mg |
| | (amount per dose) |

The above ingredients are formulated in the proportions listed above into granules.

preparation EXAMPLE 3

| | |
|---|---|
| Pivmecillinam | 70 mg |
| Compound 27 | 70 mg |
| Lactose | 33 mg |
| Crystalline cellulose | 15 mg |
| Magnesium stearate | 3 mg |
| Talc | 4 mg |
| Corn starch | 15 mg |
| Hydroxypropylmethylcellulose | 10 mg |
| Total | 220 mg |
| | (amount per tablet) |

The above ingredients are formulated in the proportions listed above into a tablet.

PREPARATION EXAMPLE 4

| | |
|---|---|
| Compound 26 | 120 mg |
| Hydroxypropylcellulose | 3 mg |
| Corn starch | 25 mg |
| Magnesium stearate | 2 mg |
| Total | 150 mg |
| | (amount per tablet) |

The above ingredients are formulated in the proportions listed above into a tablet.

What is claimed is:

1. A penicillin derivative of the formula:

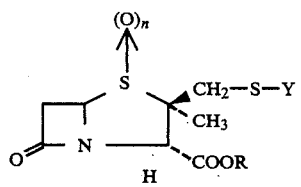

wherein n is an integer of 0, 1 or 2; Y is a cyano group, a lower acyl group, a mono- or di-lower alkylthiocarbamoyl group,

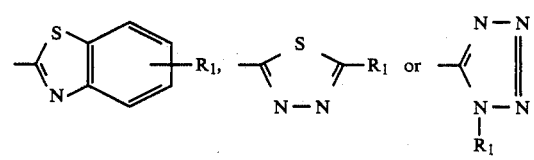

wherein $R_1$ is a hydrogen atom, a lower alkyl group, a phenyl group, a phenyl group substituted by at least one member selected from the class consisting of a lower alkyl group, halogen atom and a lower alkoxy group or a group $-(CH_2)_m-OR_2$ or $-(CH_2)_m COOR_2$ wherein m is an integer of 1 to 6 and $R_2$ is a hydrogen atom or a penicillin carboxyl ester-forming group which is commonly used for penicillin derivatives and R is a hydrogen atom or a penicillin carboxyl ester-forming group, or a pharmaceutically acceptable salt thereof.

2. A compound as claimed in claim 1 wherein Y is a cyano group, a lower acyl group, a mono- or di-lower alkylthiocarbamoyl group,

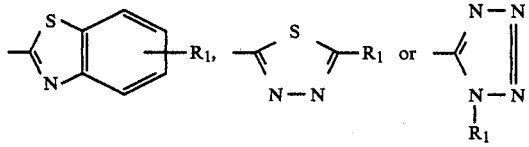

wherein R₁ is a hydrogen atom, a lower alkyl group or a phenyl group.

3. A compound as claimed in claim 1 wherein Y is

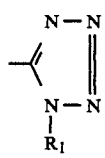

wherein R₁ is a phenyl group substituted by at least one member selected from the class consisting of halogen atom and lower alkoxy group, a group —(CH₂)ₘ—OR₂ or —(CH₂)ₘ—COOR₂ wherein m is an integer of 1 to 6 and R₂ is a hydrogen atom or a penicillin carboxyl ester-forming group which is commonly used for penicillin derivatives.

4. A compound as claimed in claim 1 wherein Y is a cyano group or

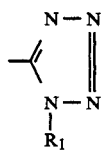

wherein R₁ is a phenyl group which may be substituted by at least one member selected from the class consisting of lower alkyl group, halogen atom and alkoxy group or a group —CH₂)ₘ—OR₂ wherein m is an integer of 1 to 6 and R₂ is a hydrogen atom or a penicillin carboxyl ester-forming group which is commonly used for penicillin derivatives.

5. A compound as claimed in claim 1, which is 2α-methyl-2β-thiocyanatomethylpenam-3α-carboxylic acid 1,1-dioxide.

6. A compound as claimed in claim 1, which is 2α-methyl-2β-(1-methyl-5-tetrazolylthio)methylpenam-3α-carboxylic acid 1,1-dioxide.

7. A compound as claimed in claim 1, which is 2α-methyl-2β-(1-p-methoxyphenyl-5-tetrazolylthio)methylpenam-3α-carboxylic acid 1,1-dioxide.

8. A compound as claimed in claim 1, which is 2α-methyl-2β-(1-phenyl-5-tetrazolylthio)methylpenam-3α-carboxylic acid 1,1-dioxide.

9. A compound as claimed in claim 1, which is 2α-methyl-2β-(1-p-chlorophenyl-5-tetrazolylthio)-methylpenam-3α-carboxylic acid 1,1-dioxide.

10. A compound as claimed in claim 1, which is 2β-[1-(2'-hydroxyethyl)-5-tetrazolylthio]methyl-2α-methylpenam-3α-carboxylic acid.

11. A method of producing a penicillin derivative of the formula:

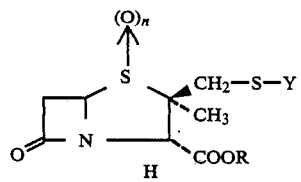

wherein n is an integer of 0, 1 or 2; Y is a cyano group, a lower acyl group, a mono- or di-lower alkylthiocarbamoyl group,

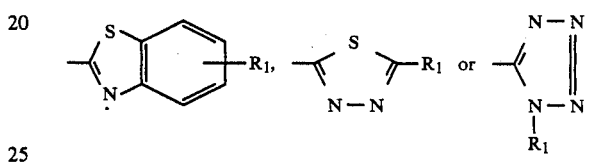

wherein R₁ is a hydrogen atom, a lower alkyl group, a phenyl group, a phenyl group substituted by at least one member selected from the class consisting of a lower alkyl group, halogen atom and a lower alkoxy group or a group —(CH₂)ₘ—OR₂ or —(CH₂)ₘ COOR₂ wherein m is an integer of 1 to 6 and R₂ is a hydrogen atom or a penicillin carboxyl ester-forming group which is commonly used for penicillin derivatives and R is a hydrogen atom or a penicillin carboxyl ester-forming group, or a pharmaceutically acceptable salt thereof, which comprises reacting a compound of the formula:

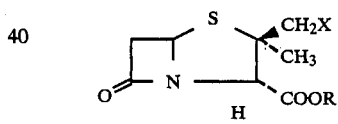

wherein X is a chlorine or bromine atom and R is as defined above with a mercapto derivative of the formula

wherein Y is as defined hereinbefore or a salt thereof to give a compound of the formula:

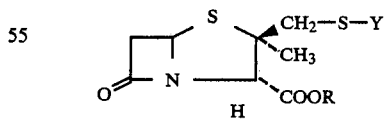

wherein Y and R are as defined hereinbefore and, if desired, subjecting the same compound to oxidation, deesterification, esterification, ester interchange or salt-forming reaction.

12. A pharmaceutical composition for treating bacterial infections in mammals comprising an antibacterial effective amount of (A) a β-lactam antibiotic, a β-lactamase inhibitory effective amount of (B) a penicillin derivative of the formula:

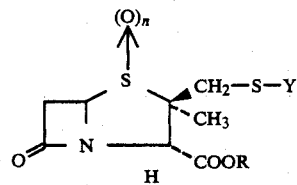

wherein n is an integer of 0, 1 or 2; Y is a cyano group, a lower acyl group, a mono- or di-lower alkylthiocarbamoyl group,

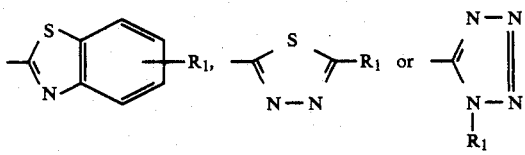

wherein $R_1$ is a hydrogen atom, a lower alkyl group, a phenyl group, a phenyl group substituted by at least one member selected from the class consisting of a lower alkyl group, halogen atom and a lower alkoxy group or a group —$(CH_2)_m$—$OR_2$ or —$(CH_2)_m COOR_2$ wherein m is an integer of 1 to 6 and $R_2$ is a hydrogen atom or a penicillin carboxyl ester-forming group which is commonly used for penicillin derivatives and R is a hydrogen atom or a penicillin carboxyl ester-forming group, or a pharmaceutically acceptable salt thereof and (C) a pharmaceutically acceptable, non-toxic carrier.

13. A pharmaceutically composition as claimed in claim 12 wherein the weight ratio of (A)/(B) is about 1 to about 10.

14. A pharmaceutical composition as claimed in claim 12 wherein the weight ratio of (A)/(B) is about 0.2 to about 5.

15. A pharmaceutical composition as claimed in claim 12 wherein the β-lactam antibiotic is ampicillin, amoxicillin, hetacillin, ciclacillin, mecillinam, carbenicillin, sulbenicillin, ticarcillin, piperacillin, apalcillin, methicillin, mezlocillin, bacampicillin, carindacillin, talampicillin, carfecillin, pivmecillinam, cephaloridine, cephalothin, cephapirin, cephacetrile, cefazolin, cephalexin, cefradine, cefotiam, cefamandole, cefuroxime, cefoxitin, cefmetazole, cefsulodin, cefoperazone, cefotaxime, ceftizoxime, cefmenoxime, latamoxef, cefaclor, cefroxadine, cefatrizine, cefadroxil or cephaloglycin, or a pharmaceutically acceptable salt thereof.

16. A pharmaceutical composition for inhibiting β-lactamase which comprises a β-lactamase inhibitory effective amount of a compound of the formula:

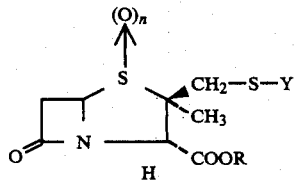

wherein n is an integer of 0, 1 or 2; Y is a cyano group, a lower acyl group, a mono- or di-lower alkylthiocarbamoyl group,

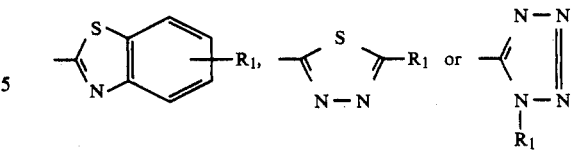

wherein $R_1$ is a hydrogen atom, a lower alkyl group, a phenyl group, a phenyl group substituted by at least one member selected from the class consisting of a lower alkyl group, halogen atom and a lower alkoxy group or a group —$(CH_2)_m$—$OR_2$ or —$(CH_2)_m COOR_2$ wherein m is an integer of 1 to 6 and $R_2$ is a hydrogen atom or a penicillin carboxyl ester-forming group which is commonly used for penicillin derivatives and R is a hydrogen atom or a penicillin carboxyl ester-forming group, or a pharmaceutically acceptable salt thereof and a pharmaceutically acceptable, non-toxic carrier.

17. A method for treating bacterial infections in mammals, which comprises administering to a mammal in need of such treatment a therapeutically effective amount of a compound as claimed in claim 1.

18. A method for treating bacterial infections in mammals, which comprises administering to a mammal in need of such treatment a therapeutically effective amount of a composition as claimed in claim 12.

19. A method for inhibiting β-lactamase in a patient in need of such treatment, said method comprising administering to said patient a therapeutically effective amount of a compound as claimed in claim 1.

20. A method for inhibiting β-lactamase in a patient in need of such treatment, said method comprising administering to said patient a therapeutically effective amount of a composition as claimed in claim 16.

21. A compound as claimed in claim 1 wherein the penicillin carboxyl ester-forming group represented by $R_2$ or R is straight-chain or branched-chain $C_1$–$C_6$ alkyl group, $C_2$–$C_7$ alkoxymethyl group, $C_{3-8}$ alkylcarbonyloxymethyl group, $C_{4-9}$ alkylcarbonyloxyethyl group, ($C_{5-7}$ cycloalkyl)carbonyloxymethyl group, $C_{9-14}$ benzylcarbonyloxyalkyl group, $C_{3-8}$ alkoxycarbonylmethyl group, $C_{4-9}$ alkoxycarbonylethyl group, halogenated $C_{1-6}$ alkyl group substituted with 1 to 3 halogen atoms, $C_{1-6}$ alkoxy- or nitro-substituted or unsubstituted benzyl group, benzhydryl, trityl, $C_{4-6}$ cyclic ether group, halogenosilyl group, (5-$C_{1-6}$ alkyl- or phenyl-substituted or unsubstituted-2-oxo-1,3-dioxoden-4-yl)methyl group, $C_{8-13}$ benzoyloxyalkyl group, lower alkylsilyl group containing 1 to 6 carbon atoms, dialkoxyalkyl group of 1 to 6 carbon atoms, phthalidyl, crotonolacton-4-yl or γ-butyrolacton-4-yl.

22. A compound as claimed in claim 3 wherein the penicillin carboxyl ester-forming group is straight-chain or branched-chain $C_1$–$C_6$ alkyl group, $C_2$–$C_7$ alkoxymethyl group, $C_{3-8}$ alkylcarbonyloxymethyl group, $C_{4-9}$ alkylcarbonyloxyethyl group, ($C_{5-7}$ cycloalkyl)carbonyloxymethyl group, $C_{9-14}$ benzylcarbonyloxyalkyl group, $C_{3-8}$ alkoxycarbonylmethyl group, $C_{4-9}$ alkoxycarbonylethyl group, halogenated $C_{1-6}$ alkyl group substituted with 1 to 3 halogen atoms, $C_{1-6}$ alkoxy- or nitro-substituted or unsubstituted benzyl group, benzhydryl, trityl, $C_{4-6}$ cyclic ether group, halogenosilyl group, (5-$C_{1-6}$ alkyl- or phenyl-substituted or unsubstituted-2-oxo-1,3-dioxoden-4-yl)methyl group, $C_{8-13}$ benzoyloxyalkyl group, lower alkylsilyl group containing 1 to 6 carbon atoms, dialkoxyalkyl group of 1 to 6 carbon atoms, phthalidyl, crotonolacton-4-yl or γ-butyrolacton-4-yl.

23. A compound as claimed in claim 4 wherein the penicillin carboxyl ester-forming group is straight-chain or branched-chain $C_1$-$C_6$ alkyl group, $C_2$-$C_7$ alkoxymethyl group, $C_{3-8}$ alkylcarbonyloxymethyl group, $C_{4-9}$ alkylcarbonyloxyethyl group, ($C_{5-7}$ cyclo alkyl)-carbonyloxymethyl group, $C_{9-14}$ benzylcarbonyloxyalkyl group, $C_{3-8}$ alkoxycarbonylmethyl group, $C_{4-9}$ alkoxycarbonylethyl group, halogenated $C_{1-6}$ alkyl group substituted with 1 to 3 halogen atoms, $C_{1-6}$ alkoxy- or nitro-substituted or unsubstituted benzyl group, benzhydryl, trityl, $C_{4-6}$ cyclic ether group, halogenosilyl group, (5-$C_{1-6}$ alkyl- or phenyl-substituted or unsubstituted-2-oxo-1,3-dioxoden-4-yl)methyl group, $C_{8-13}$ benzoyloxyalkyl group, lower alkylsilyl group containing 1 to 6 carbon atoms, dialkoxyalkyl group of 1 to 6 carbon atoms, phthalidyl, crotonolacton-4-yl or γ-butyrolacton-4-yl.

24. A method as claimed in claim 11 wherein the penicillin carboxyl ester-forming group is straight-chain or branched-chain $C_1$-$C_6$ alkyl group, $C_2$-$C_7$ alkoxymethyl group, $C_{3-8}$ alkylcarbonyloxymethyl group, $C_{4-9}$ alkylcarbonyloxyethyl group, ($C_{5-7}$ cycloalkyl)carbonyloxymethyl group, $C_{9-14}$ benzylcarbonyloxyalkyl group, $C_{3-8}$ alkoxycarbonylmethyl group, $C_{4-9}$ alkoxycarbonylethyl group, halogenated $C_{1-6}$ alkyl group substituted with 1 to 3 halogen atoms, $C_{1-6}$ alkoxy- or nitro-substituted or unsubstituted benzyl group, benzhydryl, trityl, $C_{4-6}$ cyclic ether group, halogenosilyl group, (5-$C_{1-6}$ alkyl- or phenyl-substituted or unsubstituted-2-oxo-1,3-dioxoden-4-yl)methyl group, $C_{8-13}$ benzoyloxyalkyl group, lower alkylsilyl group containing 1 to 6 carbon atoms, dialkoxyalkyl group of 1 to 6 carbon atoms, phthalidyl, crotonolacton-4-yl or γ-butyrolacton-4-yl.

25. A pharmaceutical composition as claimed in claim 12 wherein the penicillin carboxyl ester-forming group represented by $R_2$ or R is straight-chain or branched-chain $C_1$-$C_6$ alkyl group, $C_2$-$C_7$ alkoxymethyl group, $C_{3-8}$ alkylcarbonyloxymethyl group, $C_{4-9}$ alkylcarbonyloxyethyl group, ($C_{5-7}$ cyclo alkyl)carbonyloxymethyl group, $C_{9-14}$ benzylcarbonyloxyalkyl group, $C_{3-8}$ alkoxycarbonylmethyl group, $C_{4-9}$ alkoxycarbonylethyl group, halogenated $C_{1-6}$ alkyl group substituted with 1 to 3 halogen atoms, $C_{1-6}$ alkoxy- or nitro-substituted or unsubstituted benzyl group, benzhydryl, trityl, $C_{4-6}$ cyclic ether group, halogenosilyl group, (5-$C_{1-6}$ alkyl- or phenyl-substituted or unsubstituted-2-oxo-1,3-dioxoden-4-yl)methyl group $C_{8-13}$ benzoyloxyalkyl group, lower alkylsilyl group containing 1 to 6 carbon atoms, dialkoxyalkyl group of 1 to carbon atoms, phthalidyl, crotonolacton-4-yl or γ-butyrolacton4-yl.

26. A pharmaceutical composition as claimed in claim 16 wherein the penicillin carboxyl ester-forming group represented by $R_2$ or R is straight-chain or branched-chain $C_1$-$C_6$ alkyl group, $C_2$-$C_7$ alkoxymethyl group, $C_{3-8}$ alkylcarbonyloxymethyl group, $C_{4-9}$ alkylcarbonyloxyethyl group, ($C_{5-7}$ cycloalkyl) carbonyloxymethyl group, $C_{9-14}$ benzylcarbonyloxyalkyl group, $C_{3-8}$ alkoxycarbonylmethyl group, $C_{4-9}$ alkoxycarbonylethyl group, halogenated $C_{1-6}$ alkyl group substituted with 1 to 3 halogen atoms, $C_{1-6}$ alkoxy- or nitro-substituted or unsubstituted benzyl group, benzhydryl, trityl, $C_{4-6}$ cyclic group, halogenosilyl group, (5-$C_{1-6}$ alkyl- or phenyl-substituted or unsubstituted-2-oxo-1,3-dioxoden-4-yl)methyl group, $C_{8-13}$ benzoyloxyalkyl group, lower alkylsilyl group containing 1 to 6 carbon atoms, dialkoxyalkyl group of 1 to 6 carbon atoms, phthalidyl, crotonolacton-4-yl or γ-butyrolacton-4-yl.

* * * * *

UNITED STATES PATENT AND TRADEMARK OFFICE
CERTIFICATE OF CORRECTION

PATENT NO. : 4,861,768

DATED : August 29, 1989

INVENTOR(S) : TORII et al

Page 1 of 3

It is certified that error appears in the above-identified patent and that said Letters Patent is hereby corrected as shown below:

On the cover page, Item [75] should read:
--Inventors: Sigeru Torii; Hideo Tanaka; Motoaki Tanaka, all of Okayama; Shozo Yamada, Honjyo; Akira Nakai, Okayama; Hisashi Ohbayashi, Honjyo, all of Japan--.

Column 22, lines 44 to 50, the formula should read:

-- 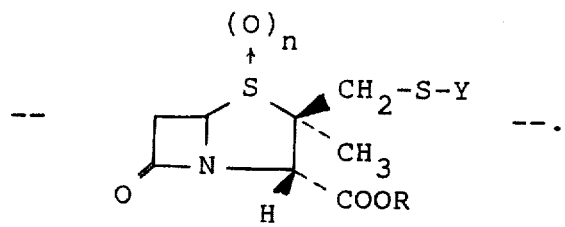 --.

Column 23, line 49, "$-CH_2)_m-OR_2$" should read -- $-(CH_2)_m-OR_2$ --.

Column 24, lines 6 to 14, the formula should read:

-- 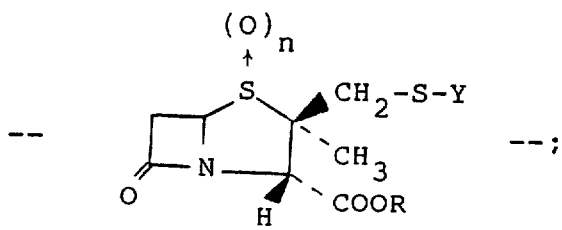 --;

lines 38 to 44, the formula should read:

-- 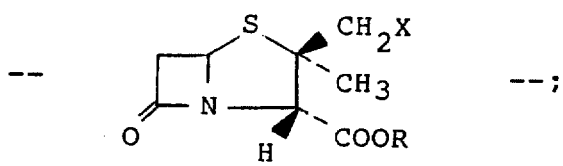 --;

UNITED STATES PATENT AND TRADEMARK OFFICE
CERTIFICATE OF CORRECTION

PATENT NO. : 4,861,768

DATED : August 29, 1989

INVENTOR(S) : TORII et al

It is certified that error appears in the above-identified patent and that said Letters Patent is hereby corrected as shown below:

Column 24, lines 53 to 59, the formula should read:

-- 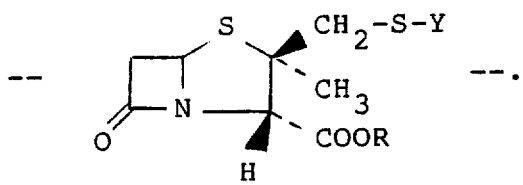 --.

Column 25, lines 1 to 5, the formula should read:

-- 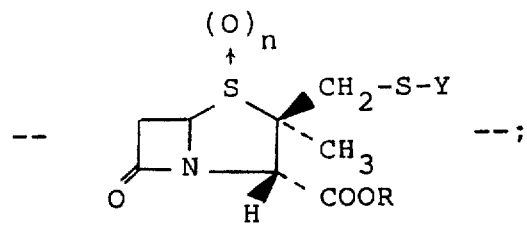 --;

line 35, "about 1" should read --about 0.1--;

UNITED STATES PATENT AND TRADEMARK OFFICE
CERTIFICATE OF CORRECTION

PATENT NO. : 4,861,768

DATED : August 29, 1989

INVENTOR(S) : TORII et al

It is certified that error appears in the above-identified patent and that said Letters Patent is hereby corrected as shown below:

Column 25, lines 57 to 64, the formula should read:

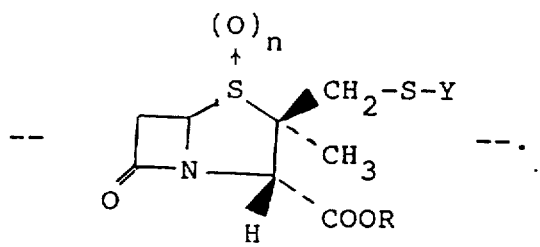

Signed and Sealed this

Twenty-second Day of January, 1991

Attest:

HARRY F. MANBECK, JR.

Attesting Officer

Commissioner of Patents and Trademarks